(12) United States Patent
Pandit

(10) Patent No.: US 7,758,522 B2
(45) Date of Patent: Jul. 20, 2010

(54) COMBINED UTERINE ACTIVITY AND FETAL HEART RATE MONITORING DEVICE

(75) Inventor: Ashit Madhusudan Pandit, Tampa, FL (US)

(73) Assignee: General Electric Company, Schenectady, NY (US)

( * ) Notice: Subject to any disclaimer, the term of this patent is extended or adjusted under 35 U.S.C. 154(b) by 50 days.

(21) Appl. No.: 11/619,500

(22) Filed: Jan. 3, 2007

(65) Prior Publication Data

US 2008/0161689 A1 Jul. 3, 2008

(51) Int. Cl.
*A61B 5/103* (2006.01)
(52) U.S. Cl. .................................... 600/591
(58) Field of Classification Search .......... 600/591, 600/485, 438, 453, 437, 443, 300
See application file for complete search history.

(56) References Cited

U.S. PATENT DOCUMENTS

| 4,966,152 | A | | 10/1990 | Gang et al. | |
|---|---|---|---|---|---|
| 5,257,627 | A | | 11/1993 | Rapoport | |
| 5,265,613 | A | * | 11/1993 | Feldman et al. | 600/453 |
| 6,171,263 | B1 | * | 1/2001 | Sullivan | 600/588 |
| 6,416,471 | B1 | * | 7/2002 | Kumar et al. | 600/300 |
| 6,816,744 | B2 | | 11/2004 | Garfield et al. | |
| 6,843,771 | B2 | * | 1/2005 | Lo et al. | 600/459 |
| 6,863,653 | B1 | * | 3/2005 | Zanelli et al. | 600/437 |

FOREIGN PATENT DOCUMENTS

WO  WO 01/78577  10/2001
WO  WO 02/96288  5/2002

OTHER PUBLICATIONS van Engelen et al., EMG Activity of the Muscular and Stromal Layer of the Cervix in Relation to EMG activity of the Myometrium and Cervical Dilation in PGF2aplha Induced Parturition in the Cow., Apr. 1, 2007, Elsevier, Theriogenology 67 (2007) 1158-1167.*
V.N.A. Breeveld-Dwarkasing, et al., Cervical Dilation Related to Uterine Electromyographic Activity and Endocrinological Changes During Prostaglandin F2α- induced Parturitioin in Cows; Oct. 23, 2003; Society for the Study of Reproduction, Biology of Reproduction vol. 68, 536-542.*

* cited by examiner

*Primary Examiner*—Max Hindenburg
*Assistant Examiner*—Fangemonique Smith
(74) *Attorney, Agent, or Firm*—Andrus, Sceales, Starke & Sawall, LLP

(57) ABSTRACT

A combinational fetal heart rate monitor and uterine activity measuring device for use on a pregnant patient. The fetal heart rate and uterine activity monitor comprising a plurality of electrodes disposed to be attached on the abdomen of the patient and an ultrasound transducers disposed to be attached on the abdomen of the patient. An energy source is operable to generate an excitation signal and the energy source is connected to a multiplexer which is connected between the plurality of electrodes and the ultrasound transducer, the multiplexer being selectively positioned to direct the excitation signal from the energy source to either the electrode or the ultrasound transducer. An amplifier connected to the energy source compares the excitation signal to the excitation signal after it passes through the abdomen of the patient. The signal from the amplifier is demodulated and processed to calculate physiological parameter based on the change in the excitation signal.

20 Claims, 5 Drawing Sheets

COMBINED UTERINE ACTIVITY AND FETAL HEART RATE MONITORING DEVICE

FIELD OF THE DISCLOSURE

The present disclosure relates to the field of non-invasive patient monitoring. Specifically, the disclosure relates to a device for the non-invasive monitoring of the uterine activity of a pregnant patient.

BACKGROUND OF THE DISCLOSURE

Prior to the onset of labor, a pregnant patient prefers to be ambulatory. In other words, the pregnant patient prefers to be able to move about freely, whether in the patient's own home, or within the hospital. However, a pregnant patient whom is likely to begin labor soon, has reduced ambulatory ability due to the number of sensors that are normally attached to their abdomen to monitor both the onset of labor as well as the health of the unborn baby.

The two most common transducers attached to the pregnant patient are transducers to monitor the fetal heart rate (FHR) and transducers to detect uterine activity (i.e. contraction). The fetal heart rate is typically monitored by a non-invasive system using a doppler ultrasound technique to detect the motion of the beating heart of the fetus. The beating heart of the fetus produces a doppler shift in the ultrasound signal received by the transducer. The doppler shift frequency is then translated into the fetal heart rate. The uterine activity of the pregnant patient is monitored using a separate device known as a tocodynamometer. The tocodynamometer uses pressure or displacement to detect uterine contractions. In one embodiment of a tocodynamometer, a pressure transducer, such as a depressible button, is affixed to the abdomen of the pregnant patient such that the pressure of the abdomen may be detected, and contractions monitored. Alternatively, the tocodynamometer may utilize a strain gauge disposed between one or more points affixed to locations on the patient's abdomen, such that the expansion and contraction of the patient's abdomen may be detected. The tocodynamometer uses the measured pressure, displacement, or strain to determine the relative strength of the contractions.

The FHR monitor and the tocodynamometer are typically held into place in a communicative relationship with the abdomen of the pregnant patient by large elastic bands that are placed around the abdomen of the patient. The elastic bands may also hold a battery pack and a transmitter, such that the FHR monitor or the tocodynamometer may be powered at a remote location, and the detected signals may be sent back to a base transmitter for recording and monitoring the FHR and uterine activity. While this system allows for the pregnant patient to be ambulatory to some extent prior to labor, typically a separate FHR monitor is needed for each fetus of the pregnancy. Therefore, a patient with a multiple fetus pregnancy may be required to have one FHR monitor attached to her abdomen per fetus of the pregnancy in addition to the tocodynamometer measuring her uterine activity. Each additional separate transducer system adds to the weight that the pregnant patient must carry around when ambulating. Furthermore, the individual monitoring devices are relatively heavy, especially the tocodynamometer. The power requirement of each of these transducers necessitates relatively larger battery packs to power the transducers which further adds additional weight. This additional weight makes the task of moving even more difficult to the pregnant patient beyond the difficulty of moving associated with the pregnancy.

Alternative embodiments comprise a combination ultrasound FHR monitor and a tocodynamometer. However, these devices suffer from the combination because the resulting combination produces a substantial weight to be held in one position on the patient's abdomen. Furthermore, the combinational systems require separate control and monitoring circuitry. This requires additional battery capacity, resulting in even more weight attached to the patient. The combination devices limit the pregnant patient's ambulation prior to labor.

Therefore, it is desirable in the field of non-invasive patient monitoring to provide a combinational fetal heart rate monitor and uterine activity monitor. It is further desirable in the field of non-invasive patient monitoring to provide a uterine activity monitor with reduced weight and power consumption needs.

SUMMARY OF THE DISCLOSURE

In an embodiment, the uterine activity monitor comprises a source of an electrical signal waveform and at least one electrode such that the electrical signal waveform is applied to the skin of a patient, such that the impedance of the patient may be monitored. The impedance of the patient is representative of the uterine activity of the pregnant patient.

In a further embodiment, a fetal heart rate monitor utilizing an ultrasound transducer is connected to the source of electrical waveform suitable for the excitation of an ultrasound crystal utilized in an ultrasonic transducer. At least one electrode is attached to the abdomen of the patient and to the source of an electrical signal waveform suitable for excitation of an ultrasound crystal. The electrical signal being applied to the skin of the patient, and the impedance of the abdomen of the patient is collected and monitored. The impedance of the abdomen of the patient is representative of the uterine activity of the patient.

In an still further embodiment, a combination fetal heart monitor and uterine activity monitor is provided where the tocodynamometer components are replaced by electrodes and the pressure for strain measurement of the tocodynamometer is replaced by an electrical measurement of impedance. The duplicative circuitry utilized for the control of separate FHR and uterine activity transducers, circuitry for monitoring and processing the signals from the transducers, and circuitry for transmitting the signal acquired by the transducers is replaced with a single set of circuitry for the control, processing, and transmission of the data.

In a still further embodiment, the FHR and uterine activity transducers are powered by a single power supply to be used in conjunction with the reduced circuitry.

DETAILED DESCRIPTION

Figure 1:
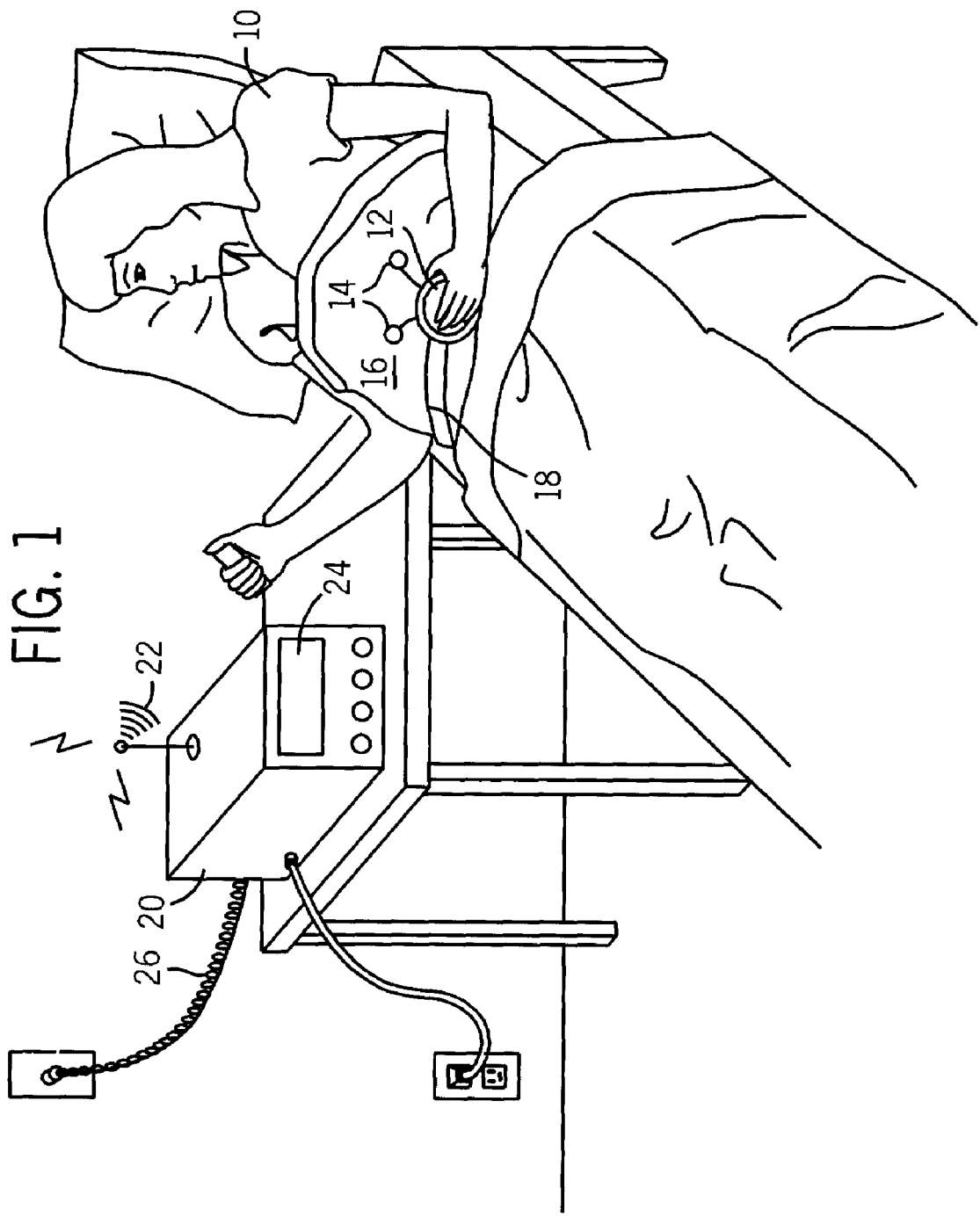
FIG. 1 depicts a patient utilizing an embodiment of a combinational uterine activity monitor and fetal heart rate monitor.

FIG. 1 depicts a pregnant patient 10 who is having her uterine activity (UA) monitor by a uterine activity (UA) monitor 12. The UA monitor 12 comprises a plurality of electrodes 14 that are attached to the abdomen 16 of the patient 10. The plurality of electrodes 14 may comprise two electrodes or four electrodes or any other suitable number of electrodes for measuring impedance. The UA monitor 12 is held in place on the abdomen 16 of the patient 10 by an elastomeric band 18. The elastomeric band 18 is attached to the UA monitor 12 and extends around the abdomen of the patient 10, thereby holding the UA monitor 12 in a secure position.

A base unit 20 may be associated with the patient 10 such that the base unit 20 may receive, process, display, or store patient physiological data that is collected by the UA monitor 12. The base unit 20 may comprise an antenna 22 to receive wireless communications from the UA monitor 12, or a wireless transmitter (not depicted) that is associated with the UA monitor 12. Alternatively, the UA monitor 12 may send data to the base unit 20 via a data cable (not depicted). The base unit 20 may further comprise a display 24 for displaying the physiological parameters monitored by the UA monitor 12 attached to the patient 10. The display 24 may display a signal that is indicative of the uterine activity of the patient 10. The base unit 20 may further be connected to a hospital network (not depicted) via a network data connection 26. The network data connection 26 may be a wired or wireless network connection that transmits data to and from the base unit 20 and a hospital data network or server. In an embodiment utilizing a hospital server or network, the base unit 20 may store physiological data collected from the patient 10 such that the physiological data may be accessed at a later time.

Figure 2:
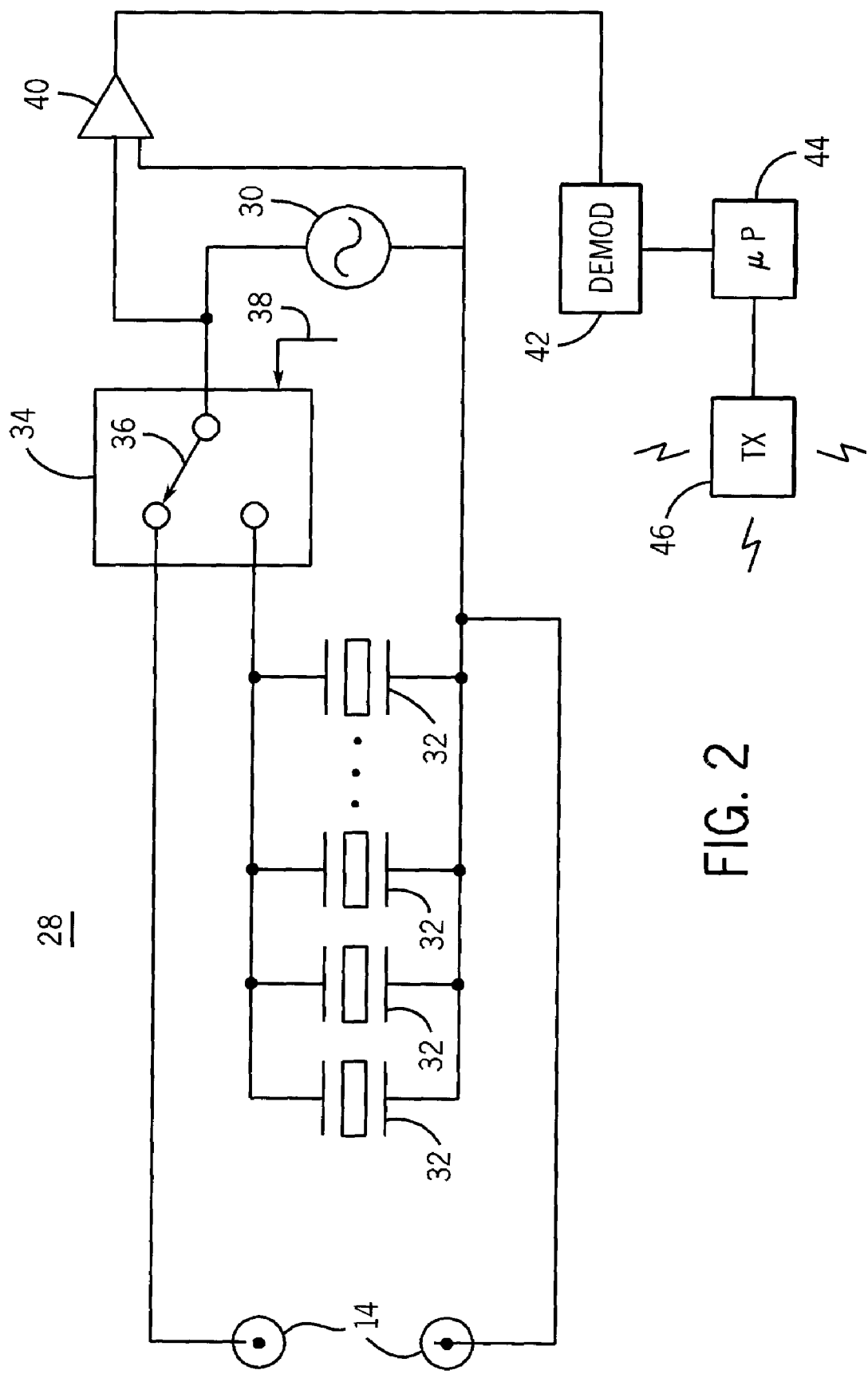
FIG. 2 is a schematic diagram of an embodiment of a combinational uterine activity and fetal heart rate monitor.

FIG. 2 depicts a schematic diagram of one embodiment of a combinational UA and FHR monitoring device 28. The combination device 28 comprises an energy source 30. The energy source 30 is connected to the electrodes 14 that are attached to the abdomen 16 of the patient 10, and a plurality of ultrasound crystals 32 that may be disposed within the monitoring device 28 in such a position that when the monitoring device 18 is held in contact with the abdomen 16 of the patient 10, the ultrasound crystals 32 are held in communication with the abdomen 16 of the patient 10. The ultrasound crystals 32 may be in communication with the abdomen 16 of the patient 10 by means of an intermediary (not depicted) such as an ultrasound coupling gel. The energy source 30 may be any type of energy source that is suitable for generating an excitation signal for energizing the plurality of ultrasound crystals 32 such that a usable ultrasound signal may be obtained therefrom. In the embodiment illustrated, the energy source 30 comprises a waveform generator generating a sine wave. In an example, the excitation signal produced by the energy source 30 is a six volt peak-to-peak sine wave at 1.15 MHz. In a further embodiment, the 1.15 MHz sine wave produces a burst frequency from the ultrasound crystals 32 between 2 kHz-4 kHz. While the examples are merely exemplary of values for the excitation signal and the ultrasound crystal burst frequency, many other values may be used in clinical settings with the excitation signal and the ultrasound burst frequency being coordinated to produce a desirable signal from the ultrasound transducer. The same excitation signal produced by the energy source 30 and applied to the ultrasound crystals 32 is also applied to at least one of the electrodes 14 attached to the patient's abdomen 16.

As shown in FIG. 2, the monitoring device 28 comprises a multiplexer 34 that is connected to the energy source 30 and comprises a switch 36 that may be selectively connected to the electrode 14 attached to the patient's abdomen 16 or alternatively to the plurality of ultrasound crystals 32. The switch 36 of the multiplexer 34 may be manually actuated or may receive an input signal 38 that directs the multiplexer 34 to switch between the electrodes 14 for monitoring uterine activity and the ultrasound crystals 32 for monitoring the fetal heart rate. The input signal 38 may be a clock signal or a pulse train at a frequency representative of the multiplexing rate.

The signal from the transducer (either the electrodes 14 or the ultrasound crystals 32) that is currently selected by the multiplexer 34 is sent to a differential amplifier 40. The amplifier 40, by itself or arranged with additional circuitry (not depicted), generates an output signal that is the differential voltage across the transducer. As depicted in FIG. 2, the switch 36 of the multiplexer 34 is shown connecting the energy source 30 and the amplifier 40 to the electrodes 14 such that the uterine activity of the patient 10 may be monitored. The excitation signal from the energy source 30 is applied to one of the electrodes 14. The differential voltage between the two electrodes 14 is indicative of the impedance of the tissue of the abdomen 16 of the patient 10 between the electrodes 14. The differential voltage, as monitored by amplifier 40, may then be sent to a demodulator 42.

When the patient 10 experiences a uterine contraction, the impedance of the patient's abdomen 16 between the electrodes 14 increases. This increase in impedance results in an amplitude modulation (AM) that is detected by the demodulator 42. The demodulator 42 removes the underlying sinusoidal excitation signal produced by the energy source 30 from the differential voltage generated by the amplifier 40. The resulting demodulated voltage thus varies with the uterine activity of the patient 10.

The demodulated voltage obtained from the demodulator 42 may be sent to a microprocessor 44 for further processing. The microprocessor 44 may comprise an analog to digital converter or a filter or filters, such as a low pass filter (LPF) or a band pass filter (BPF), for processing the demodulated signal. Alternatively, the A/D converter and/or any filters may be separate components (not depicted) between the demodulator 42 and the microprocessor 44. After the uterine activity signal has been processed by the microprocessor 44, the signal may be sent to a transmitter 46 such that the transmitter 46 can transmit the patient physiological data representative of the uterine activity of the patient from the transmitter 46 to the antenna 22 of the base unit 20 where the physiological data may be displayed, processed, or stored by the base unit 20.

In an alternative operation, switch 36 is positioned such that they energy source 30 is connected to the ultrasound crystals 32. When in this position, the ultrasound crystals 32 receive the excitation signal from energy source 30 and the amplifier 40 will receive signals indicative of the received ultrasound signals. The received ultrasound signals include a doppler frequency shift representative of the fetal heart rate. The ultrasound signals are similarly demodulated by demodulator 42 and processed by microprocessor 44 to calculate the fetal heart rate, which may be transmitted by the transmitter 46 to the base unit 20.

Figure 3:
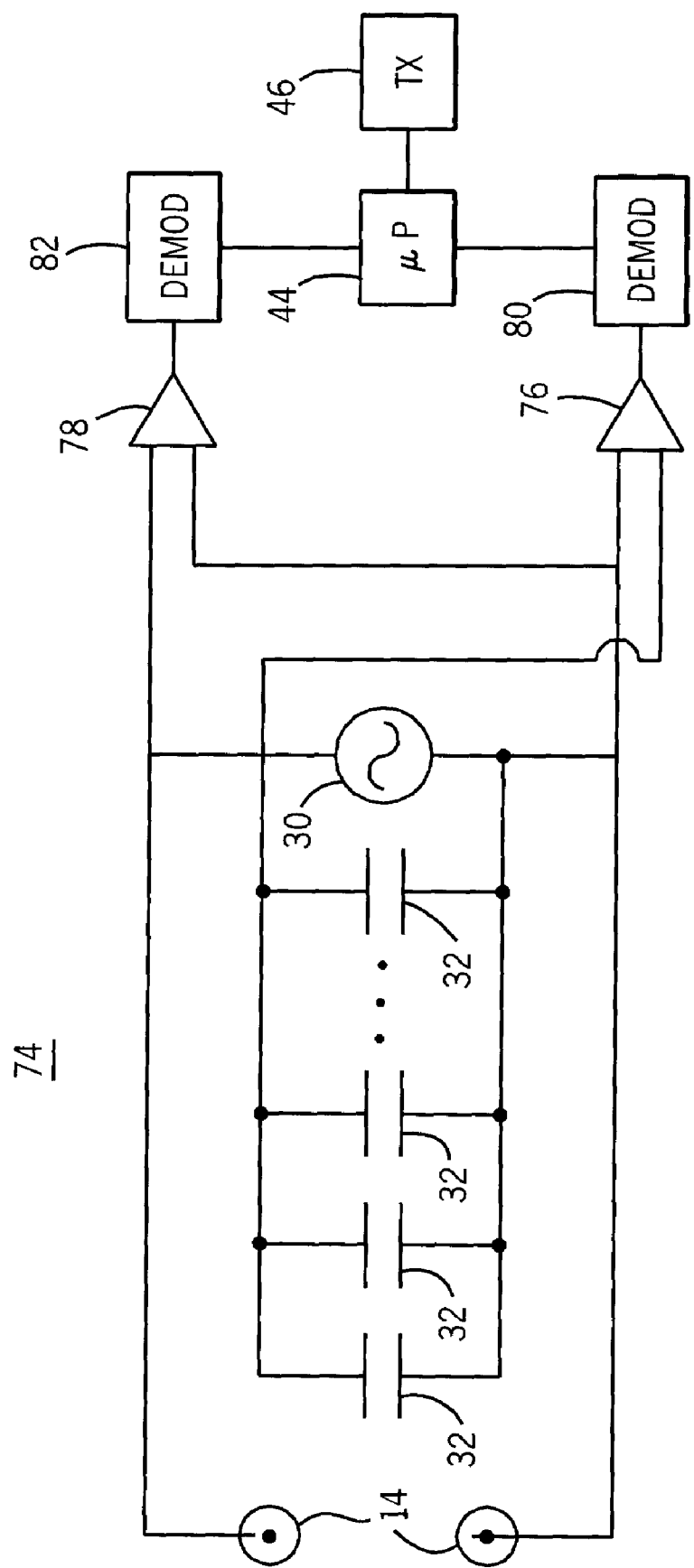
FIG. 3 is a schematic diagram of an alternative embodiment of a combinational uterine activity and fetal heart rate monitor.

FIG. 3 is a schematic diagram representing an alternative embodiment of the circuitry of a combinational UA and FHR monitoring device 74. Similar to the monitoring device 28 depicted in FIG. 2, the monitoring device 74 comprises an energy source 30 that produces an excitation signal. The excitation signal is supplied to the electrodes 14 that are attached to the abdomen of the patient. The excitation signal is also provided to the plurality of ultrasound crystals 32 that are also attached to the abdomen of the patient. However, in the monitoring device 74, the multiplexer 34 has been eliminated in favor of separate signal processing circuitry for the detection of the signals from the electrodes 14 and the ultrasound crystals 32. A first amplifier 78 is connected to the electrodes 14 and monitors the electrical signal through the patient's abdomen that is indicative of the impedance changes in the patient's abdomen. The first amplifier 78 produces a differential signal that is sent to first demodulator 82 and the demodulated signal is provided to a common microprocessor 44.

A second amplifier 76 is attached to the plurality of ultrasound crystals 32 such that the second amplifier 76 produces a differential voltage indicative of the return signal received by the ultrasound transducers 32. This differential signal is provided to the second demodulator 80 and the demodulated signal is provided to the common microprocessor 44. The common microprocessor 44 may then perform signal processing functions on the demodulated impedance signal and the demodulated ultrasound signal to calculate signals indicative of the uterine activity and the fetal heart rate.

The uterine activity and fetal heart rate signals may be transmitted back to the base unit 20 via the transmitter 46. In an alternative embodiment, additional electronic components may be used in the circuitry between the demodulators 80 and 82 and the common microprocessor 44. The additional electronic circuitry may comprise low pass filters, band pass filters, or A/D converters (not depicted) that may perform additional precursor signal processing before the signals are received by the common microprocessor 44. An advantage of the monitoring device 74 depicted in FIG. 3 is that both the uterine activity signal has calculated from the signal from the electrodes 14 and the fetal heart rate which is calculated from the signal from the ultrasound crystals 32 are obtained simultaneously, and may be obtained continuously, without the need to multiplex the collection of each physiological signal.

Figure 4:
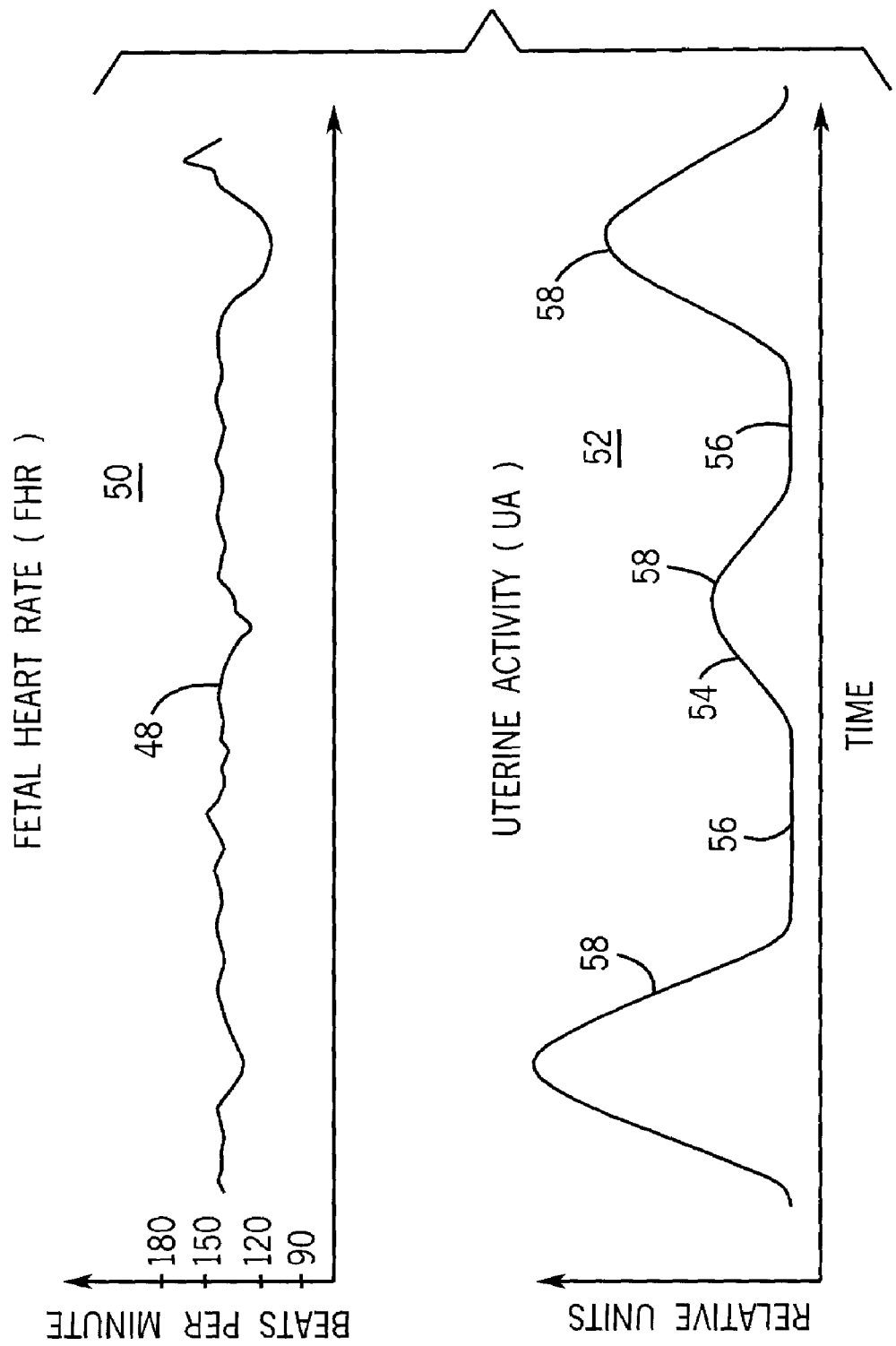
FIG. 4 depicts a graphical representation of a generic output from a combinational fetal heart rate monitor and uterine activity monitor.

FIG. 4 is a graph representing the physiological data as processed from the signals recorded from the patient 10 by the electrodes 14 and the ultrasound crystals 32. The ultrasound crystals 32 are used to detect fetal heart rate, which is represented as the line 48 on the fetal heart rate graph 50. The doppler frequency shift in the received ultrasound signal is indicative of the fetal heart rate. The fetal heart rate 48 typically ranges between 120-150 beats per minute for a healthy fetus. The uterine activity graph 52 depicts the uterine activity as represented by line 54. The uterine activity is measured in relative units from a normal, average, or baseline uterine activity level 56, which is opposed to period of contraction 58 when the uterine activity is at an increased level in comparison to the baseline 56 uterine activity level. This baseline uterine activity level 56 may be calibrated individually to each pregnant patient by any processing algorithms, or alternatively a standardized baseline may be used.

Figure 5:
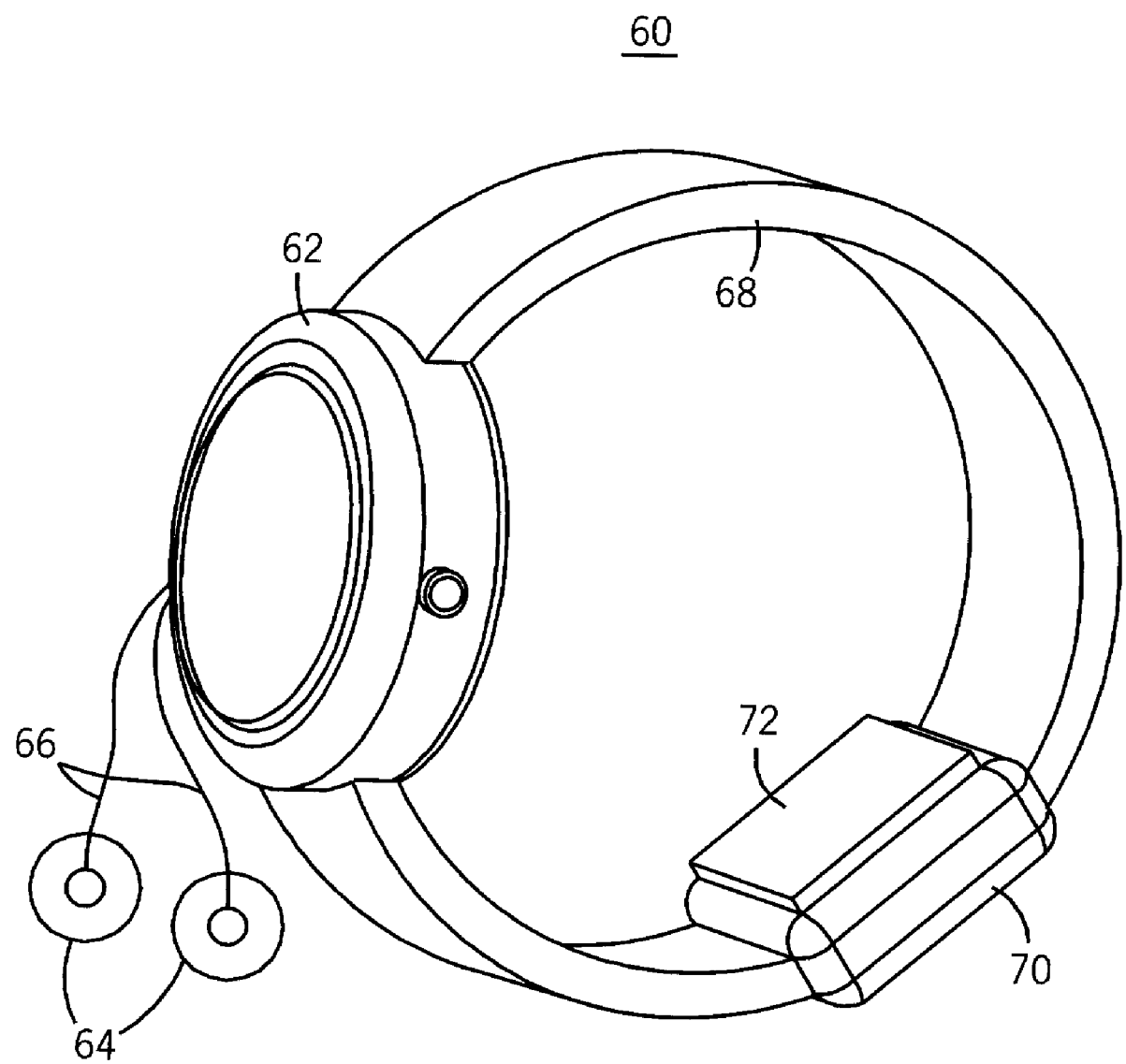
FIG. 5 depicts an embodiment of a uterine activity monitor and fetal heart rate monitor.

FIG. 5 depicts an embodiment of a monitoring device 60 to be worn by an ambulating pregnant patient. The monitoring device 60 comprises an outer casing 62. The outer casing 62 may be formed out of a plastic or any other suitable material for housing transducers and electronics to be held in contact with the skin of a patient. Disposed within the outer casing 62 are the electronics (not depicted) and at least one transducer for monitoring a physiological parameter of the patient. In an embodiment, the electronics disposed within the casing 62 may comprise all or some of the electronics represented in the schematic diagrams of FIGS. 2 and 3. Furthermore, the transducer disposed within the outer casing 62 may be a plurality of ultrasound crystals that are arranged such that the crystals are in contact with the abdomen of the patient when the monitoring device 60 is worn around the abdomen of the patient. A pair of electrodes 14 may be connected to the circuitry disposed within the casing 62 by a pair of lead wires 64. In an alternative embodiment, more than two electrodes are utilized to monitor uterine activity, and as such the plurality of electrodes 14 comprises additional electrodes.

The monitoring device 60 further comprises an elastomeric band 68. The elastomeric band 68 is fixedly attached to the outer casing 62 such that the elastomeric band may be fitted around the body of the patient 10 such that the monitoring device 60 is held in the proper position over the abdomen 16 of the patient 10. The accuracy of the monitoring of fetal heart rate by ultrasound Doppler shift frequency is dependent upon proper placement of the ultrasound crystals and the crystals being held in communication with the skin of the patient. Therefore, the elastomeric band 68 holds the ultrasound crystals disposed within the outer casing 62 in the proper position for obtaining a measurement of the fetal heart rate. The outer casing 62 may further compromise an ultrasound coupling material (not depicted), such as an ultrasound coupling gel, for enhancing the communication between the ultrasound crystals and the patient's abdomen 16. The elastomeric band 68 may comprise any material with elastomeric properties such, but not limited to, rubber, elastic, or neoprene.

The monitoring device 60 may further comprise a power source 70. The power source 70 may comprise a battery or battery pack; furthermore, the battery may comprise a plurality of disposable and/or rechargeable/reusable cells. The power supply 70 is suitable for supplying power to the circuitry disposed within the outer casing 62 for the collection and processing of the uterine activity and fetal heart rate measurements as obtained by the electrodes and the ultrasound transducer. Furthermore, the power supply 70 is such that it supplies the power to all of the electronics within the monitoring device 60 and additional sources of power and/or batteries are not needed. The monitoring device 60 may further comprise a transmitter 72. The transmitter 72 is suitable for transmitting the monitored physiological data from the monitoring device 60 back to a base unit 20 for the display, storing, or further processing of the physiological data. The transmitter 72 may comprise RF transmitting technology, or may utilize other short range forms of data transmission such as Bluetooth or infrared; however, these examples are merely exemplary and are not intended to be limiting on the scope of transmitter to be used in the accordance with this disclosure.

Aspects of embodiments described within this disclosure comprise certain advantages in the field of non-invasive patient monitoring. In embodiments in this disclosure a uterine activity monitor and a fetal heart rate monitor are combined into a single monitoring device. The combination of these two monitoring devices into a single device combines two of the most commonly used monitoring devices for monitoring the health of a pregnant patient and her fetus, therefore the combination of these two monitoring devices is desired in the field. Furthermore the additional weight, and bulk of two separate monitoring devices is reduced into the packaging of only a single monitoring device with a single power supply. Furthermore, further power efficiency and space efficiency may be gained by the use of common monitoring, processing, and transmitting electronics for both of the transducers within the monitoring device.

In further embodiments in this disclosure, a bulky and weighty tocodynamometer is eliminated from the monitoring device and the specialized circuitry needed to operate and process the signals received from the tocodynamometer are also eliminated. In embodiments disclosed in this disclosure, the tocodynamometer is replaced by a pair of light weight electrodes that utilize less power than the tocodynamometer and may be efficiently combined with the circuitry for the operation of the ultrasound transducer for the monitoring of fetal heart rate, such that a lighter weight and more power efficient monitoring device is produced.

This written description uses examples to disclose features of the embodiments, including the best mode, and also to enable any person skilled in the art to make and use the invention. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

Various alternatives and embodiments are contemplated as being with in the scope of the following claims, particularly pointing out and distinctly claiming the subject matter regarded as the invention.

What is claimed is:

1. A fetal heart rate and uterine activity monitor the monitor comprising:
   a plurality of electrodes disposed to be attached to the abdomen of the patient;
   a plurality of ultrasound crystals disposed to be held in communication with the abdomen of the patient;
   an energy source operable to generate an excitation signal, the energy source being connected to both the plurality of electrodes and the plurality of ultrasound crystals to provide the excitation signal to the electrodes and the ultrasound crystals;
   an impedance monitor including a first amplifier connected to the plurality of electrodes, the first amplifier producing a signal representative of the impedance of the abdomen of the patient and a first demodulator connected to the first amplifier, the first demodulator calculating the change in amplitude of the signal from the first amplifier;
   a fetal heart rate monitor including a second amplifier connected to the plurality of ultrasound crystals, the second amplifier producing a signal representative of the difference between the excitation signal applied to the plurality of ultrasound crystals and the acoustical return received by the ultrasound crystals and a second demodulator connected to the second amplifier, the second demodulator calculating the change in amplitude of the signal from the second amplifier; and
   a processor that receives a signal from the first demodulator indicative of the impedance of the abdomen of the patient and calculates the uterine activity of the patient and receives a signal from the second demodulator and calculates the fetal heart rate.

2. The device of claim 1 wherein the energy source produces a sine wave excitation signal.

3. The device of claim 2 further comprising a transmitter that receives a signal indicative of the uterine activity and the fetal heart rate and transmits the signal to a base station for the display of the uterine activity and fetal heart rate.

4. The device of claim 3 further comprising:
   a first analog to digital converter connected between the first demodulator and the processor, the first analog to digital converter converting a first analog signal from the first demodulator to a first digital signal provided to the processor; and
   a second analog to digital convert connected between the second demodulator and the processor, the second analog to digital converter converting a second analog signal from the second demodulator to a second digital signal provided to the processor.

5. The device of claim 3, further comprising an outer casing, the casing encapsulating the energy source, the first amplifier, the second amplifier, the first demodulator, the second demodulator, and the processor.

6. The device of claim 5, further comprising a single power source for supplying power to the energy source, impedance monitor, and the fetal heart rate monitor.

7. The device of claim 1, wherein the plurality of electrodes are two electrodes, the energy source being connected to both of the electrodes and the first amplifier being connected to both of the electrodes.

8. A method of monitoring the uterine activity of a pregnant patient, the method comprising:
   attaching a plurality of electrodes to the abdomen of the patient;
   attaching an ultrasound transducer to the abdomen of the patient;
   generating an excitation signal suitable for the excitation of an ultrasound crystal;
   alternately directing the excitation signal to energize either the plurality of electrodes or the ultrasound transducers;
   wherein the excitation or signal is directed to the plurality of electrodes;
   energizing at least one of the electrodes with the excitation signal;
   monitoring at least one of the electrodes to obtain the excitation signal after the excitation signal has passed through the patient's abdomen;
   demodulating the excitation signal to measure the impedance of the patient's abdomen;
   calculating the uterine activity of the patient based on the measured impedance;
   and wherein when the excitation signal is directed to the ultrasound transducer:
   energizing the ultrasound transducer with the excitation signal;
   monitoring the ultrasound transducer to obtain a ultrasound signal;
   demodulating the ultrasound signal to obtain a signal representative of the heart rate of the fetus; and
   calculating the fetal heart rate.

9. The method of claim 8 wherein the steps of energizing the at least one electrode and the step of energizing the ultrasound transducer are performed using the same excitation signal produced by an energy source.

10. The method of claim 9 wherein the uterine activity and the fetal heart rate are alternatively monitored and calculated.

11. The method of claim 9, wherein at least one of the electrodes and the ultrasound transducer are energized simultaneously;
    at least one of the electrodes and the ultrasound transducer are monitored simultaneously; and
    the uterine activity and the fetal heart rate are calculated simultaneously.

12. A combinational fetal heart rate monitor and uterine activity measuring device for use on a pregnant patient, the device comprising:
    an energy source that generates an excitation signal;
    an impedance monitor including a plurality of electrodes attached to the abdomen of the patient, the electrodes connected to the energy source to receive the excitation signal;
    a fetal heart rate monitor including an ultrasound transducer attached to the abdomen of the patient, the ultrasound transducer connected to the energy source to receive the excitation signal;

a processor connected to the impedance monitor and the fetal heart rate monitor, the processor calculating uterine activity when a signal is received from the impedance monitor and calculating the fetal heart rate when a signal is received from the fetal heart rate monitor; and a multiplexer connected between the energy source and both the electrodes and the ultrasound transducer, the multiplexer being selectively positioned to direct the excitation signal from the energy source to selectively between the electrodes and the ultrasound transducer;

wherein if the multiplexer is positioned to direct the excitation signal to the electrodes, the processor receives a signal from the electrodes and if the multiplexer is positioned to direct the excitation signal to the ultrasound transducer, the processor receives a signal from the ultrasound transducer.

13. The device of claim 12, further comprising a common amplifier connected to the impedance monitor and the fetal heart rate monitor, the common amplifier amplifying a signal from one of the impedance monitor and the fetal heart rate monitor and directing an amplified signal to the processor.

14. The device of claim 12, further comprising a common demodulator connected to the impedance monitor and the fetal heart rate monitor, the common demodulator demodulating a signal from one of the impedance monitor and the fetal heart rate monitor and directing a demodulated signal to the processor.

15. The device of claim 13, further comprising a common demodulator connected to the impedance monitor and the fetal heart rate monitor through the common amplifier, the common demodulator demodulating the amplified signal from the common amplifier and directing a demodulated signal to the processor.

16. The device of claim 12, wherein the plurality of electrodes are two electrodes, wherein when the multiplexer is positioned to direct the excitation signal to the electrodes, the excitation signal is applied to one of the two electrodes.

17. The device of claim 12, further comprising an outer casing, the outer casing encapsulating the energy source, the multiplexer, the amplifier, the demodulator and the processor.

18. The device of claim 17, further comprising an elastomeric belt, the elastomeric belt disposed to secure the device to the abdomen of the patient.

19. The device of claim 12, further comprising a single power source for supplying power to the energy source, the impedance monitor, and the fetal heart rate monitor device.

20. The device of claim 19, wherein the single power source is a battery pack, the battery pack being secured to an elastomeric belt.

\* \* \* \* \*